(12) United States Patent
Kamee

(10) Patent No.: US 9,341,344 B2
(45) Date of Patent: May 17, 2016

(54) ILLUMINATION APPARATUS

(71) Applicant: OLYMPUS CORPORATION, Tokyo (JP)

(72) Inventor: Hiroyuki Kamee, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/556,691

(22) Filed: Dec. 1, 2014

(65) Prior Publication Data

US 2015/0085469 A1 Mar. 26, 2015

Related U.S. Application Data

(63) Continuation of application No. PCT/JP2013/063707, filed on May 16, 2013.

(30) Foreign Application Priority Data

Jun. 1, 2012 (JP) .................................. 2012-126308

(51) Int. Cl.
*F21V 13/08* (2006.01)
*F21V 9/16* (2006.01)
(Continued)

(52) U.S. Cl.
CPC ............. *F21V 13/08* (2013.01); *A61B 1/00096* (2013.01); *A61B 1/0653* (2013.01); *A61B 1/0661* (2013.01); *F21V 9/16* (2013.01); *G02B 6/0003* (2013.01); *G02B 6/0008* (2013.01); *G02B 23/2469* (2013.01); *G03B 15/05* (2013.01); *F21Y 2101/00* (2013.01);
(Continued)

(58) Field of Classification Search
CPC ............. A61B 1/00096; A61B 1/0653; A61B 1/0661; F21V 9/16; F21V 13/08; F21Y 2101/00; G02B 6/0003; G02B 6/0008; G02B 23/2469; G03B 15/05; G03B 2215/0582
See application file for complete search history.

(56) References Cited

U.S. PATENT DOCUMENTS 8,358,067 B2 * 1/2013 Kamee ................. G02B 6/0008
313/583
8,801,204 B2 * 8/2014 Kamee ...................... F21V 9/16
362/84

(Continued)

FOREIGN PATENT DOCUMENTS

JP 59-58418 U 4/1984
JP 2009-003228 A 1/2009
(Continued)

OTHER PUBLICATIONS

International Search Report dated Jul. 30, 2013 issued in PCT/JP2013/063707.
(Continued)

*Primary Examiner* — Stephen F Husar
(74) *Attorney, Agent, or Firm* — Scully, Scott, Murphy & Presser, P.C.

(57) ABSTRACT

An illumination apparatus includes a light source unit which emits primary light, and an optical unit which functions when the primary light emitted from the light source unit is applied to the optical unit. The optical unit includes a reducing portion which is directly provided in a illumination light emitting portion or provided frontward to part of the illumination light emitting portion and which reduces the density of the primary light as the illumination light emitted from the illumination light emitting portion.

12 Claims, 12 Drawing Sheets

(51) Int. Cl.
*A61B 1/06* (2006.01)
*G02B 23/24* (2006.01)
*F21V 8/00* (2006.01)
*G03B 15/05* (2006.01)
*A61B 1/00* (2006.01)
*F21Y 101/00* (2016.01)

(52) U.S. Cl.
CPC . *G03B2215/0564* (2013.01); *G03B 2215/0582* (2013.01)

(56) References Cited

U.S. PATENT DOCUMENTS 9,134,010 B2 * 9/2015 Ito .................. A61B 1/0661
2009/0040598 A1 2/2009 Ito
2014/0098547 A1 * 4/2014 Kostelnik ............ H03K 17/955
362/311.02

FOREIGN PATENT DOCUMENTS

| | | |
|---|---|---|
| JP | 2009-043668 A | 2/2009 |
| JP | 2011-123368 A | 6/2011 |

OTHER PUBLICATIONS

International Preliminary Report on Patentability together with the Written Opinion dated Dec. 11, 2014 from related International Application No. PCT/JP2013/063707, together with an English language translation.

* cited by examiner

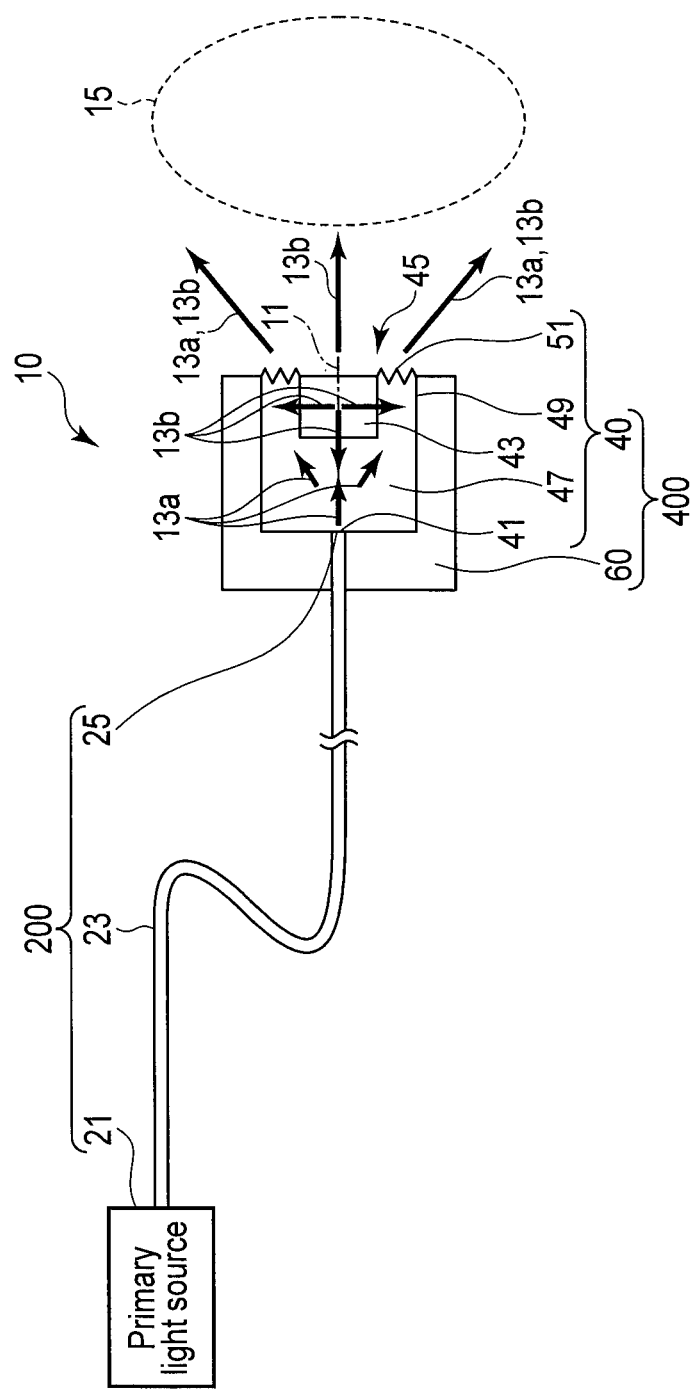
F I G. 1

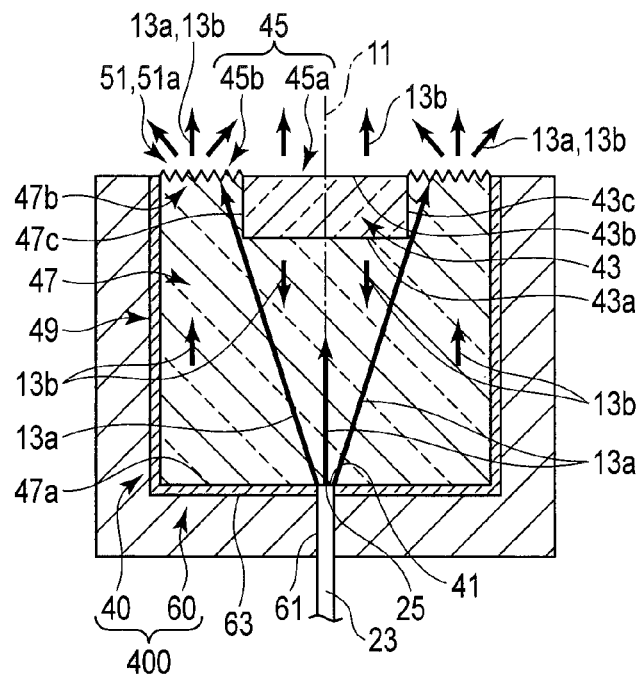
F I G. 2A
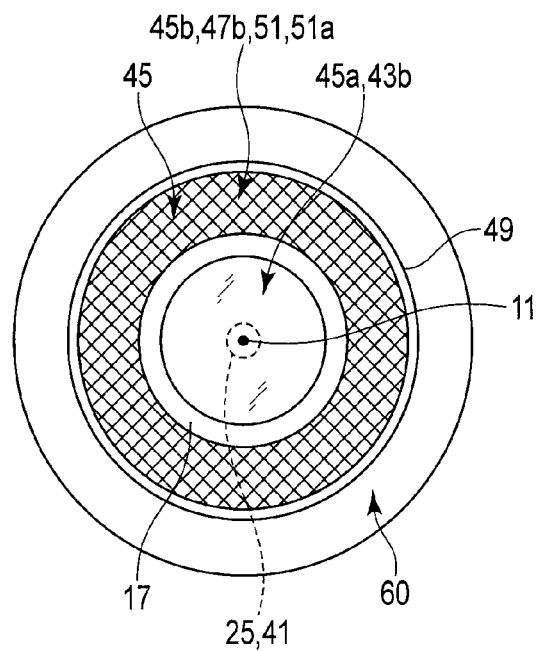
F I G. 2B

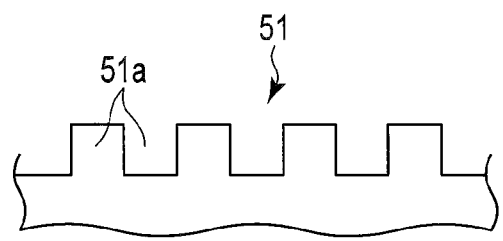
F I G. 3A
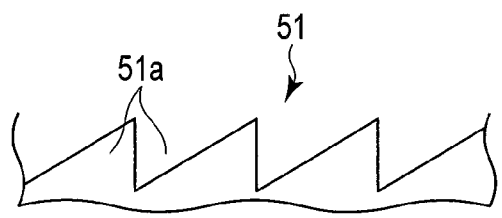
F I G. 3B
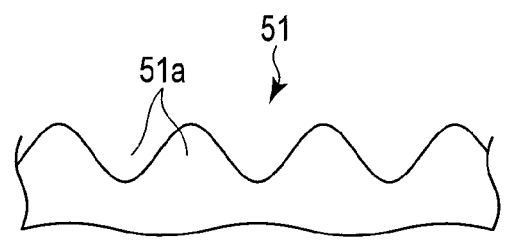
F I G. 3C
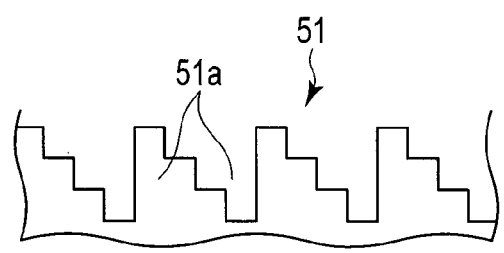
F I G. 3D

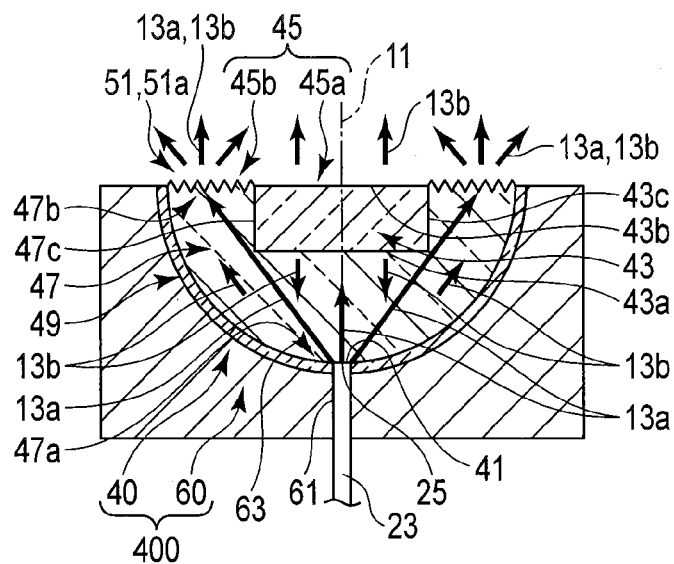
F I G. 5B
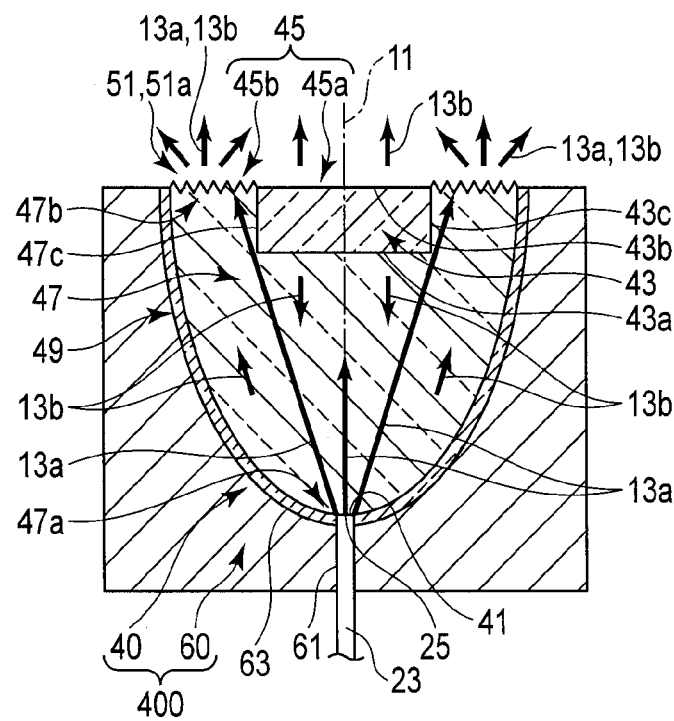
F I G. 5C

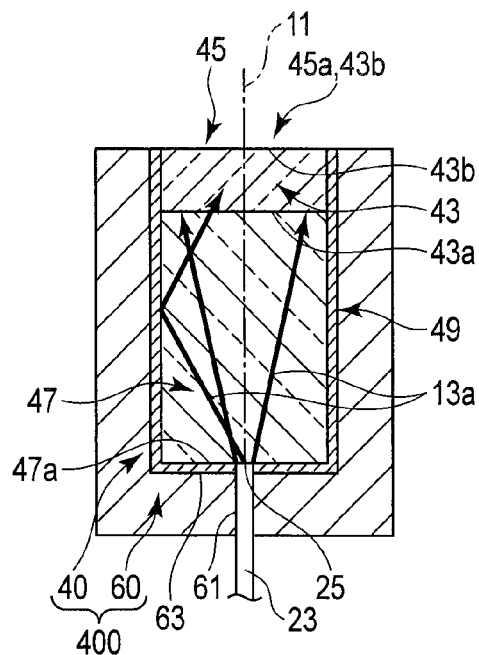
F I G. 11B
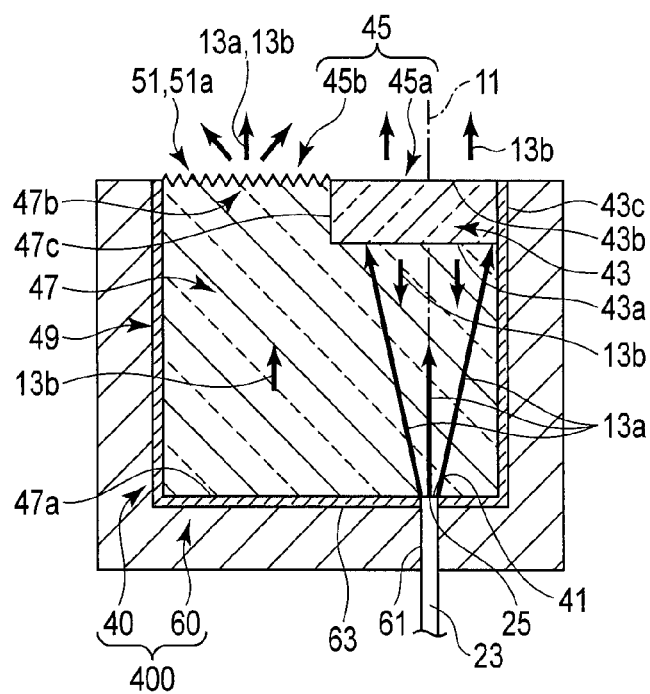
F I G. 11C

ILLUMINATION APPARATUS

CROSS-REFERENCE TO RELATED APPLICATIONS

This application is a Continuation application of PCT Application No. PCT/JP2013/063707, filed May 16, 2013 and based upon and claiming the benefit of priority from prior Japanese Patent Application No. 2012-126308, filed Jun. 1, 2012, the entire contents of all of which are incorporated herein by reference.

BACKGROUND OF THE INVENTION

1. Field of the Invention

The present invention relates to an illumination apparatus which evenly illuminates an illumination target.

2. Description of the Related Art

Recently, a fiber light source having a small solid-state light source and an optical fiber has been developed. This fiber light source is combined with an imaging unit. This fiber light source is used as an illumination apparatus which emits light from the distal end portion of an elongated structure. This fiber light source is disclosed in, for example, Jpn. Pat. Appln. KOKAI Publication No. 2009-3228. Jpn. Pat. Appln. KOKAI Publication No. 2009-3228 discloses a long-life and high-output light emitting apparatus in which a solid-state light source is used.

In this light emitting apparatus, the small solid-state light source is connected to a light guide member such as an optical fiber, and the distal end portion of the light guide member is held by a holding member. A wavelength converting member such as a fluorescent material is provided at the distal end portion of the light guide member. A spacer is provided between the distal end portion of the light guide member and the wavelength converting member. This spacer has a through-hole portion. A metallic thin film which is a reflecting portion is provided on the circumferential surface of the through-hole portion. Some of the light emitted from the wavelength converting member functions as rearward emission light which is emitted from the wavelength converting member to the side of the light guide member.

The above-mentioned thin film reflects the rearward emission light toward the wavelength converting member so that the rearward emission light returns to the wavelength converting member. As a result, the rearward emission light is used as illumination light.

In Jpn. Pat. Appln. KOKAI Publication No. 2009-3228, the wavelength converting member covers the whole portion emission side opening portion of the spacer. This ensures that the light emitted from the light guide member enters the wavelength converting member. This also ensures that the rearward emission light is reflected by the thin film and enters the wavelength converting member again.

However, in general, the wavelength converting member has a scattering function to scatter some of wavelength-converted light having its wavelength converted by this wavelength converting member, or an absorption function to absorb the wavelength-converted light. Therefore, the light which is normally emitted to the outside is scattered by the wavelength converting member and absorbed by some other member. The light which is normally emitted to the outside is absorbed by the wavelength converting member. Accordingly, the amount of light is reduced. Thus, sufficient efficiency of light usage is not ensured.

The present invention has been made in view of these circumstances, and is intended to provide an illumination apparatus which can ensure sufficient efficiency of light usage.

BRIEF SUMMARY OF THE INVENTION

An aspect of an illumination apparatus including a light source unit which emits primary light, and an optical unit which functions when the primary light emitted from the light source unit is applied to the optical unit, the light source unit comprising a primary light emitting portion which emits the primary light to the optical unit, the optical unit comprising: a primary light entrance portion which is optically connected to the primary light emitting portion and which the primary light emitted from the primary light emitting portion enters; a light converting member which is provided apart from the primary light entrance portion, the light converting member converting the optical characteristics of the primary light entering from the primary light entrance portion when the primary light is applied to the light converting member, the light converting member generating secondary light different from the primary light; an illumination light emitting portion which emits at least one of the primary light and the secondary light to an outside as illumination light; the central axis of the primary light emitted by the primary light emitting portion being referred to as an optical axis, the side of the primary light emitting portion in an optical axis direction being referred to as rearward, the side of the light converting member in the optical axis direction being referred to as frontward, a direction that intersects at right angles with the optical axis being referred to as sideward, a light transmitting member which is provided between the primary light entrance portion and the light converting member and which is also at least partly continuously provided from the primary light entrance portion to the illumination light emitting portion so that the primary light and the secondary light is transmitted therethrough; a reflecting portion which is provided on a circumferential surface of the light transmitting member including the light converting member and which reflects the primary light and the secondary light; and a reducing portion which is directly provided in the illumination light emitting portion or provided frontward to part of the illumination light emitting portion and which reduces the density of the primary light as the illumination light emitted from the illumination light emitting portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram of an illumination apparatus according to a first embodiment of the present invention;

FIG. 2A is a diagram showing how primary light travels in an optical unit;

FIG. 2B is a diagram of the optical unit shown in FIG. 2A viewed from the side of an illumination light emitting portion;

FIG. 3A is a diagram showing an example of the shape of an indented portion;

FIG. 3B is a diagram showing an example of the shape of the indented portion;

FIG. 3C is a diagram showing an example of the shape of the indented portion;

FIG. 3D is a diagram showing an example of the shape of the indented portion;

FIG. 5B is a diagram showing an example of the optical unit according to the first modification of the first embodiment;

FIG. 5C is a diagram showing an example of the optical unit according to the first modification of the first embodiment;

FIG. 11B is a sectional view taken along the line 11B-11B shown in FIG. 11A;

FIG. 11C is a sectional view taken along the line 11C-11C shown in FIG. 11A;

DETAILED DESCRIPTION OF THE INVENTION

Figure 4:
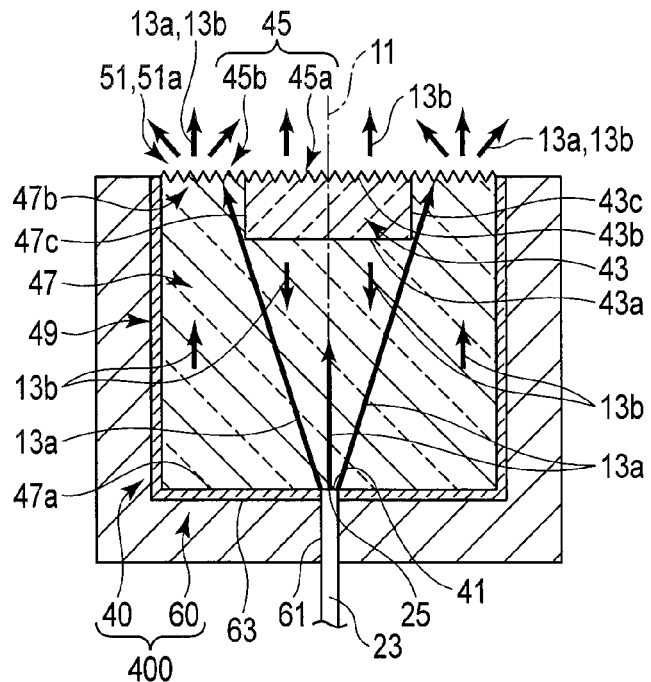
FIG. 4 is a diagram showing the optical unit in which a reducing portion is also formed in a first emission portion.

Hereinafter, embodiments of the present invention will be described in detail with reference to the drawings. In some of the drawings, some components are not shown for clarity.

[First Embodiment]

[Configuration]

The first embodiment is described with reference to FIG. 1, FIG. 2A, and FIG. 2B.

The central axis of primary light 13a emitted by a primary light emitting portion 25 is hereinafter referred to as an optical axis 11.

In an optical axis direction, the side of the primary light emitting portion 25 is referred to as rearward, the side of a light converting member 43 is referred to as frontward, and a direction that intersects at right angles with the optical axis 11 is referred to as sideward.

[Illumination Apparatus 10]

As shown in FIG. 1, an illumination apparatus 10 has a light source unit 200 which emits primary light 13a, and an optical unit 400 which functions when the primary light 13a emitted from the light source unit 200 is applied to the optical unit 400.

[Light Source Unit 200]

As shown in FIG. 1, the light source unit 200 has a primary light source 21 which emits the primary light 13a that is, for example, excitation light, and an unshown condensing lens which condenses the primary light 13a emitted from the primary light source 21. As shown in FIG. 1, the light source unit 200 also has an optical fiber 23 serving as a light guide member which the primary light 13a condensed by the condensing lens enters and which guides the primary light 13a toward the optical unit 400, and the primary light emitting portion 25 which is provided at the end portion of the optical fiber 23 and which emits, to the optical unit 400, the primary light 13a guided by the optical fiber 23.

[Primary Light Source 21]

The primary light source 21 shown in FIG. 1 has a point light source having the following characteristics: for example, emitting the primary light 13a having a high straight traveling property, being high in the efficiency of the entry of the primary light 13a into the optical fiber 23, being high in the efficiency of energy use, being low in power consumption, and being small in size. The primary light source 21 emits the primary light 13a which causes excitation and light generation in the light converting member 43 of the optical unit 400. This primary light source 21 has, for example, a semiconductor laser light source which emits blue laser light. The primary light source 21 is optically connected to the optical fiber 23 via the unshown condensing lens.

[Optical Fiber 23]

As shown in FIG. 1, the optical fiber 23 has, for example, softness and flexibility. The optical fiber 23 is also, for example, bendable. The optical fiber 23 has, for example, an elongated columnar shape. The optical fiber 23 has optical properties which allow the primary light 13a to be highly efficiently guided. The optical fiber 23 is made of, for example, glass or plastic. The optical fiber 23 has, for example, a multifiber mode optical fiber 23. The core diameter of the optical fiber 23 is, for example, 50 μm, and the numerical aperture NA of the optical fiber 23 is 0.2. The optical fiber 23 has optical properties which allow the primary light 13a to be highly efficiently guided frontward so that the primary light 13a is emitted frontward from the primary light emitting portion 25 without any great energy loss. In this instance, the emission angle of the primary light 13a is determined by the numerical aperture of the optical fiber 23 and the refractive index of a later-described light transmitting member 47.

[Primary Light Emitting Portion 25]

As shown in FIG. 1, the primary light emitting portion 25 functions as an emission surface which emits the primary light 13a, and functions as the end face of the optical fiber 23. The primary light emitting portion 25 has a shape corresponding to the sectional shape of the optical fiber 23. Since the optical fiber 23 has a columnar shape, the primary light emitting portion 25 has, for example, a circular shape.

[Optical Unit 400]

The optical unit 400 has an optical element 40 which functions when the primary light 13a emitted from the primary light emitting portion 25 is applied thereto, and a holding portion 60 which holds the optical element 40 so that it covers the side surface and rear surface of the optical element 40.

[Configuration of Optical Element 40]

As shown in FIG. 1, the optical element 40 has a primary light entrance portion 41 which is optically connected to the primary light emitting portion 25 and which the primary light 13a emitted from the primary light emitting portion 25 enters. The optical element 40 also has the light converting member 43 which is provided apart from the primary light entrance portion 41, converts the optical characteristics of the primary light 13a entering from the primary light entrance portion 41 when the primary light 13a is applied to the light converting member 43 and generates secondary light 13b different from the primary light 13a. The optical element 40 also has an illumination light emitting portion 45 which emits at least one of the primary light 13a and the secondary light 13b to an outside illumination target 15 as illumination light.

As shown in FIG. 1, the optical element 40 also has the light transmitting member 47 which is provided between the primary light entrance portion 41 and the light converting member 43 and which is also at least partly continuously provided from the primary light entrance portion 41 to the illumination light emitting portion 45 so that the primary light 13a and the secondary light 13b can be transmitted therethrough. The optical element 40 also has a reflecting portion 49 which is provided on the circumferential surface of the light transmitting member 47 including the light converting member 43 and which reflects the primary light 13a and the secondary light 13b.

As shown in FIG. 1, the optical element 40 also has a reducing portion 51 which is directly provided in the illumination light emitting portion 45 and which reduces the density of the primary light 13a as the illumination light emitted from the illumination light emitting portion 45.

These components included in the optical element 40 have concentric shapes around the optical axis 11, and are provided rotationally symmetrically with respect to the optical axis 11.

[Primary Light Entrance Portion 41]

As shown in FIG. 2A, the primary light entrance portion 41 is formed in a part of a rear surface 47a of the light transmitting member 47 on which the primary light emitting portion 25 abuts. More specifically, in the light transmitting member 47, a part of the rear surface 47a to which the primary light emitting portion 25 is optically connected is formed as the primary light entrance portion 41. This rear surface 47a represents a plane provided, for example, on the rearmost side of the light transmitting member 47 in the optical axis direction. The primary light entrance portion 41 is provided on the optical axis 11, and formed on the central axis of the light transmitting member 47. The primary light entrance portion 41 has substantially the same shape and area as the primary light emitting portion 25 (the diameter of the core of the optical fiber 23).

[Light Converting Member 43]

The light converting member 43 absorbs, for example, the primary light 13a, and then converts the wavelength of the absorbed primary light 13a to a wavelength different from that of the primary light 13a. The light converting member 43 then generates the secondary light 13b having this wavelength. Thus, the light converting member 43 functions as a wavelength converting member which converts the wavelength of the primary light 13a, and functions as an optical element which functions when the primary light 13a is applied thereto.

As shown in FIG. 2A, the light converting member 43 faces the primary light emitting portion 25 and the primary light entrance portion 41 so that the primary light 13a is applied to the light converting member 43, and the light converting member 43 is provided frontward to the primary light emitting portion 25 and the primary light entrance portion 41. In this instance, the light converting member 43 is provided so that the central axis of the light converting member 43 is provided on the optical axis 11.

As shown in FIG. 2A, the light converting member 43 has, for example, a columnar shape. Therefore, the light converting member 43 has a circular rear surface 43a facing the primary light emitting portion 25 and the primary light entrance portion 41, a circular front surface 43b provided frontward to the rear surface 43a, and a curved side surface 43c which is a circumferential surface provided between the rear surface 43a and the front surface 43b.

As shown in FIG. 2A, the rear surface 43a and the front surface 43b have the same size. The rear surface 43a and the front surface 43b are planes provided to intersect at right angles with the optical axis 11. The central axes of the rear surface 43a and the front surface 43b are provided on the optical axis 11.

As shown in FIG. 2A, in the direction of the optical axis 11, the rear surface 43a is provided apart from the primary light emitting portion 25 and the primary light entrance portion 41. The size of the rear surface 43a and the distance from the rear surface 43a to the primary light emitting portion 25 and the primary light entrance portion 41 will be described later. The rear surface 43a functions as an application surface to which the primary light 13a is applied.

As shown in FIG. 2A, the front surface 43b functions as a first emitting portion 45a which emits the primary light 13a and the secondary light 13b as the illumination light. The front surface 43b is exposed to, for example, the outside.

As shown in FIG. 2A, in the direction that intersects at right angles with the optical axis 11, the side surface 43c is provided apart from the reflecting portion 49. For example, the light transmitting member 47 is provided sideward to the side surface 43c. For example, the light transmitting member 47 is provided rearward to the rear surface 43a. The side surface 43c abuts on the light transmitting member 47 together with the rear surface 43a.

This light converting member 43 is made of, for example, a fluorescent material. When the illumination light emitting portion 45 emits, for example, white illumination light, the light converting member 43 includes several kinds of powder fluorescent materials and an optically transparent resin. In this instance, the several kinds of powder fluorescent materials are dispersed into the resin in combination with one another, and the resin is solidified in this state so that the light converting member 43 is shaped. In this case, for example, the mean particle diameter of the powder fluorescent materials is about 8 μm, the resin is an optically transparent silicone resin, and the concentration of the resin is 5 wt %.

The thickness of the light converting member 43 and the above-mentioned concentration are set to a desired thickness and concentration depending on how much of the primary light the light converting member 43 converts into the secondary light 13b. In the present embodiment, the optical unit 400 emits the primary light 13a and the secondary light 13b. Thus, the thickness and the above-mentioned concentration of the light converting member 43 are such that the light converting member 43 does not fully absorb the primary light 13a and so that the light converting member 43 converts some of the primary light 13a to the secondary light 13b.

[Illumination Light Emitting Portion 45]

As shown in FIG. 2A and FIG. 2B, the illumination light emitting portion 45 has the first emitting portion 45a which is provided in the light converting member 43 and which emits the primary light 13a and the secondary light 13b as the illumination light, and a second emitting portion 45b which is provided in the light transmitting member 47 and which emits the primary light 13a and the secondary light 13b as the illumination light. The first emitting portion 45a and the second emitting portion 45b are exposed to the outside.

[First Emitting Portion 45a]

As shown in FIG. 2A and FIG. 2B, the first emitting portion 45a functions as the circular front surface 43b of the light converting member 43, as described above. The central axis of the first emitting portion 45a is provided on the optical axis 11. The first emitting portion 45a is provided in a region other than the second emitting portion 45b.

[Second Emitting Portion 45b]

As shown in FIG. 2A and FIG. 2B, the second emitting portion 45b functions as a front surface 47b of the light transmitting member 47. The second emitting portion 45b is provided so that some of the primary light 13a which has entered from the primary light entrance portion 41 directly travels to the second emitting portion 45b. The second emitting portion 45b is provided in a region where the primary light that has entered from the primary light entrance portion 41 enters straight via the light transmitting member 47 alone and where the primary light can reach without entering any components (e.g., the reflecting portion 49) other than the light transmitting member 47. As shown in FIG. 2B, the second emitting portion 45b has an annular belt shape (ring shape). This second emitting portion 45b surrounds the first emitting portion 45a so that a inner circumferential edge of the second emitting portion 45b comes into close contact with an outer circumferential edge of the first emitting portion 45a and so that the first emitting portion 45a is flush with the second emitting portion 45b. As shown in FIG. 2A and FIG. 2B, the second emitting portion 45b is provided sideward of the first emitting portion 45a.

The first emitting portion 45a and the second emitting portion 45b form the circular illumination light emitting portion 45 of the optical element 40 which is arranged as above are provided in the optical element 40 and emits the primary light 13a and the secondary light 13b as the illumination light.

[Configuration of Light Transmitting Member 47]

As shown in FIG. 2A, the light transmitting member 47 has the rear surface 47a having a part which functions as the primary light entrance portion 41, and the front surface 47b which is provided frontward to the rear surface 47a and which functions as the second emitting portion 45b. The rear surface 47a and the front surface 47b are planes provided to intersect at right angles with the optical axis 11. The central axes of the rear surface 47a and the front surface 47b are provided on the optical axis 11. The front surface 43b is exposed to the outside.

The original shape of the light transmitting member 47 has, for example, a columnar shape. In the present embodiment, the actual shape of the light transmitting member 47 has, for example, a depressed columnar shape.

More specifically, as shown in FIG. 2A, the light transmitting member 47 has a depression 47c into which the light converting member 43 fits so that the front surface 43b of the light converting member 43 is flush with the front surface 47b of the light transmitting member 47 and so that the central axis of the light transmitting member 47 and the central axis of the light converting member 43 are provided on the optical axis 11. The depression 47c is provided in the front surface 47b of the light transmitting member 47. Thus, the rear surface 47a of the light transmitting member 47 has a circular shape, and the front surface 47b has an annular belt shape (ring shape).

In other words, as shown in FIG. 2A, the light transmitting member 47 has the light converting member 43 so that the light transmitting member 47 surrounds the rear surface 43a and the side surface 43c of the light converting member 43, so that the rear surface 43a is located apart from the primary light emitting portion 25 and the primary light entrance portion 41, so that the second emitting portion 45b is flush with the first emitting portion 45a and exposed to the outside, and so that the central axis of the light transmitting member 47 and the central axis of the light converting member 43 are provided on the optical axis 11.

The light transmitting member 47 is provided between the primary light emitting portion 25 and the light converting member 43 so that the rear surface 43a of the light converting member 43 is located apart from the primary light emitting portion 25 and the primary light entrance portion 41 and so that the light converting member 43 and the reflecting portion 49 are located apart from each other. Thus, in the present embodiment, the light transmitting member 47 is formed all around the side of the light converting member 43 continuously from the primary light entrance portion 41 to the second emitting portion 45b so that the light transmitting member 47 fills the space between the light converting member 43 and the reflecting portion 49.

[Optical Characteristics of Light Transmitting Member 47]

The light transmitting member 47 is made of a material which transmits the primary light 13a entering from the primary light entrance portion 41 and the secondary light 13b entering from the light converting member 43. Such a material includes, for example, an optically transparent material with high transmissivity. This material includes, for example, a silicone resin, glass, or quartz.

[Reflecting Portion 49]

As shown in FIG. 2A, the reflecting portion 49 is provided so that it surrounds the light transmitting member 47 around the optical axis 11. More specifically, the reflecting portion 49 is provided, for example, on the rear surface 47a of the light transmitting member 47 except for the primary light entrance portion 41, and on the side surface of the light transmitting member 47. Thus, the reflecting portion 49 is provided apart from the light converting member 43. The reflecting portion 49 is also provided so that it does not to reflect, toward the optical fiber 23 side, the primary light 13a traveling to the light transmitting member 47 from the primary light entrance portion 41. The reflecting portion 49 has a function to regularly reflect or diffusely reflect visible light.

In the present embodiment, the reflecting portion 49 is formed by the formation of a film of, for example, a metal. In this case, it is preferable that a reflective material is vapor-deposited over a sample masked by a front surface 49a and the primary light entrance portion 41 or that the sample is plated with the reflective material. The reflective material is preferably a metallic material which can be easily formed on the side surface and which has high reflectivity for visible light. The reflective material is particularly preferably aluminum or silver.

[Reducing Portion 51]

The primary light 13a emitted from the second emitting portion 45b needs to be evenly applied to the illumination target 15 so that the illumination apparatus 10 obtains satisfactory illumination light. Thus, the reducing portion 51 reduces the density of the primary light 13a emitted from the second emitting portion 45b. Therefore, as shown in FIG. 2A, the reducing portion 51 does not emit the primary light 13a in a near-parallel-light state, but sufficiently diffuses the primary light 13a to the outside (toward the illumination target 15 side) and emits the primary light 13a so that the distribution of the primary light 13a is expanded. Thus, the reducing portion 51 functions as an angle increasing portion which increases the emission angle of the primary light 13a.

As shown in FIG. 2A and FIG. 2B, the reducing portion 51 is formed over the entire second emitting portion 45b representing the front surface 47b of the light transmitting member 47. Thus, the reducing portion 51 is exposed to the outside. The reducing portion 51 is provided directly in the illumination light emitting portion 45. Moreover, the reducing portion 51 is provided in the second emitting portion 45b which is located sideward of the first emitting portion 45a, and has an annular belt shape (ring shape).

As shown in FIG. 2A and FIG. 2B, the reducing portion 51 has a small indented portion 51a provided for the diffusion of the primary light 13a. It is preferable that the average angle of an inclined plane formed by the indented portion 51a is sharp for sufficient diffusion of the primary light 13a.

For example, the indented portion 51a may be formed with a regular height and arrangement or formed with an irregular height and arrangement. When the indented portion 51a is irregularly formed, the indented portion 51a is produced, for example, by blowing metallic powder to the surface of the second emitting portion 45b or by using a chemical treatment to corrode the surface of the second emitting portion 45b.

The indented portion 51a may have, for example, a grating structure (diffractive optical lattice structure) which induces a diffractive interference phenomenon. In this way, a regular optical path difference is formed in the indented portion 51a, the primary light 13a transmitted through the indented portion 51a interferes, and a condition in which interference is reinforced in a direction inclined from the optical axis 11 is created. The second emitting portion 45b emits the primary light 13a so that the distribution of the primary light 13a is expanded while maintaining high transmissivity.

The indented portion 51a has a pitch and a height of, for example, 0.2 μm to 100 μm. This indented portion 51a has at least two of, for example, a rectangular shape shown in FIG. 3A, a saw-tooth shape shown in FIG. 3B, a sinusoidal shape shown in FIG. 3C, and a stepped shape shown in FIG. 3D. The indented portion 51a is formed by, for example, one of a mechanical manufacturing method, a holographic method, and nanoprint technology. The mechanical manufacturing method means a method whereby the surface of the second emitting portion 45b is mechanically scratched by a rigid material such as diamond. The holographic method means a method whereby a resist is exposed by the interference of parallel light beams in two directions and patterned. The nanoprint technology means a method whereby a micro-fabricated shape is transferred to the surface of the second emitting portion 45b.

If the primary light 13a is emitted in a particular direction alone, color shading of the illumination light is maintained. Thus, in the case of the diffractive optical lattice structure, it is preferable that the indented portion 51a has a structure in which at least one of the pitch and height is regularly or irregularly arranged and in which different interference conditions are repeated. Alternatively, it is preferable that the indented portion 51a is formed by the combination of at least two of the rectangular shape shown in FIG. 3A, the saw-tooth shape shown in FIG. 3B, the sinusoidal shape shown in FIG. 3C, and the stepped shape shown in FIG. 3D.

The indented portion 51a may have a structure closely packed with small lens shapes on the surface, that is, a microlens group. In this case, the indented portion 51a is formed into a spherical or elliptically spherical shape of several μm to several hundred μm for ease of manufacturing the indented portion 51a.

As described above, the reducing portion 51 is formed by the fabrication of the second emitting portion 45b, and is integral with the light transmitting member 47.

[Holding Portion 60]

The holding portion 60 is made of, for example, a metallic or plastic material that is easily processed with precision and that is not easily deformed. This metal includes, for example, ceramics and stainless steel. The holding portion 60 may be made of a material having a heat radiation effect. The holding portion 60 is made of a material that does not absorb the primary light 13a and the secondary light 13b.

As shown in FIG. 2A, the holding portion 60 holds the primary light emitting portion 25 and the light transmitting member 47 having the light converting member 43 so that the primary light emitting portion 25 and the light transmitting member 47 are positioned, so that the primary light emitting portion 25 is optically connected to the primary light entrance portion 41, and so that the relative distance between the primary light entrance portion 41 and the light converting member 43 is fixed.

Therefore, the holding portion 60 has a columnar first hollow portion 61 into which the primary light emitting portion 25 is fitted, and, for example, a columnar second hollow portion 63 in the same shape as the light transmitting member 47 having the light converting member 43 so that the light transmitting member 47 is fitted into the second hollow portion 63. The first hollow portion 61 and the second hollow portion 63 are in commutation with the outside.

The central axis of the first hollow portion 61 and the central axis of the second hollow portion 63 are provided on the central axis of the holding portion 60. The first hollow portion 61 is in commutation with the second hollow portion 63 in the optical axis direction so that the primary light emitting portion 25 is optically connected to the primary light entrance portion 41. The first hollow portion 61 is provided rearward to the second hollow portion 63.

[Relation between Size of Beam Spot 17 and Size of Rear Surface of Light Converting Member 43]

In the present embodiment, as shown in FIG. 2A and FIG. 2B, a beam spot 17 is formed by the primary light 13a emitted from the primary light emitting portion 25, and represents an application region of the primary light 13a projected on a plane that intersects at right angles with the optical axis 11. Particularly in the present embodiment, the beam spot 17 represents an application region projected on a plane that intersects at right angles with the optical axis 11 including the rear surface 43a of the light converting member 43. The primary light emitting portion 25 has, for example, a circular shape, and the beam spot 17 has a circular shape around the optical axis 11 because of the characteristics of the general optical fiber 23. The beam spot 17 is defined as a region which is irradiated by at least an intensity higher than $1/e^2$ of the maximum intensity of the primary light 13a. e is Napier's constant as a base of a natural logarithm.

The general beam spot 17 is equal in light distribution around the optical axis 11, and has a Gaussian intensity distribution shape in a direction inclined relative to the optical axis 11.

In the present embodiment, as shown in FIG. 2A and FIG. 2B, the beam spot 17 is formed to be larger than the rear surface 43a of the light converting member 43 so that the primary light 13a is emitted from the second emitting portion 45b and then illuminates the illumination target 15 as a part of the illumination light. Therefore, the rear surface 43a is provided apart from the primary light emitting portion 25 and the primary light entrance portion 41 so that the beam spot 17 is formed to be larger than the rear surface 43a.

It is preferable that the relative distances between the primary light emitting portion 25, the primary light entrance portion 41, the light converting member 43, and the reflecting portion 49 are positioned such that the primary light 13a is reflected by the reflecting portion 49 and does not enter the light converting member 43, so that the primary light 13a is reflected by the reflecting portion 49 and is not emitted from second emitting portion 45b, so that the secondary light 13b emitted from the rear surface 43a and the side surface 43c is reflected by the reflecting portion 49 and emitted from the second emitting portion 45b as illumination light without entering the light converting member 43 again, and so that some of the primary light 13a directly travels to the second emitting portion 45b.

[Function]

The primary light 13a is emitted from the primary light source 21, and highly efficiently condensed in the optical fiber 23 by the condensing lens. The primary light 13a is guided to the primary light emitting portion 25 by the optical fiber 23, and then emitted from the primary light emitting portion 25. In this instance, the emission angle of the primary light 13a is determined by, for example, the numerical aperture of the optical fiber 23 and the refractive index of the light converting member 43.

As shown in FIG. 2A, the primary light 13a enters the primary light entrance portion 41, and is then transmitted through the light transmitting member 47. As described above, the rear surface 43a of the light converting member 43 is provided apart from the primary light emitting portion 25 and the primary light entrance portion 41. Thus, some of the primary light 13a is applied to the entire rear surface 43a of the light converting member 43, and the rest of the primary light 13a directly travels to the second emitting portion 45b.

Some of the primary light 13a is converted to the secondary light 13b by the light converting member 43. The secondary light 13b is emitted from the light converting member 43 in various directions.

For example, the secondary light 13b is emitted to the outside from the first emitting portion 45a as illumination light, and is applied to the illumination target 15.

For example, the secondary light 13b is also emitted from the side surface 43c, transmitted through the light transmitting member 47 and then emitted from the second emitting portion 45b as illumination light, and applied to the illumination target 15.

For example, the secondary light 13b is also emitted from the rear surface 43a and the side surface 43c, transmitted through the light transmitting member 47 and then reflected by the reflecting portion 49, emitted from the second emitting portion 45b as illumination light, and applied to the illumination target 15.

Most of the secondary light 13b is emitted from the rear surface 43a of the light converting member 43. This is because most of the primary light 13a is applied to the rear surface 43a so that most of the primary light 13a is converted to the secondary light in the vicinity of the rear surface 43a and then the secondary light is isotropically emitted. In addition, the light converting member 43 having the functions to diffuse and absorb the secondary light 13b is provided frontward to the rear surface 43a, while the light transmitting member 47 only having the transmitting function is provided rearward to the rear surface 43a, so that most of the isotropically emitted secondary light is redistributed rearward. Most of the secondary light 13b is reflected by the reflecting portion 49 provided on the side of the rear surface 47a of the light transmitting member 47 more than one time. Some of the reflected secondary light 13b directly travels to the second emitting portion 45b without entering the light converting member 43. This secondary light 13b is then emitted from the second emitting portion 45b as illumination light, and applied to the illumination target 15.

The rest of the primary light 13a directly travels to the second emitting portion 45b. In the second emitting portion 45b, owing to the reducing portion 51, the primary light 13a is not emitted in a near-parallel-light state, but is sufficiently diffused to the outside (toward the illumination target 15), and is emitted so that the distribution of the primary light 13a is expanded. Thus, the density of the primary light 13a is reduced, and the primary light 13a is evenly applied to the illumination target 15 as illumination light.

[Advantageous Effects]

In the present embodiment, owing to the reducing portion 51, the primary light 13a can be sufficiently diffused to the outside (toward the illumination target 15), and emitted so that the distribution of the primary light 13a is expanded. Accordingly, in the present embodiment, the density of the primary light 13a can be reduced, and the primary light 13a can be evenly applied to the illumination target 15 as illumination light. In the present embodiment, the secondary light 13b can also be applied to the illumination target 15. Thus, in the present embodiment, the primary light 13a and the secondary light 13b can be used as illumination light, and it is therefore possible to provide the illumination apparatus 10 which ensures sufficient efficiency of light usage.

In the present embodiment, some of the secondary light 13b emitted from the rear surface 43a and the side surface 43c of the light converting member 43 can be applied to the illumination target 15 as illumination light from the second emitting portion 45b without entering the light converting member 43 again, owing to the reflecting portion 49. That is, some of the primary light 13a and some of the secondary light 13b can be emitted from the second emitting portion 45b provided sideward of the light converting member 43 to sneak through the light converting member 43. These effects are referred to as sneak-through effects. In the present embodiment, the reduction of the amount of the secondary light 13b as the illumination light can be prevented by the optical characteristics of the light converting member 43 and the optical characteristics of the reflecting portion 49. Thus, in the present embodiment, it is possible to provide the illumination apparatus 10 which permits a high extraction efficiency of the secondary light 13b.

In the present embodiment, the secondary light 13b is emitted more from the rear surface 43a than from the circular front surface 43b and the side surface 43c. However, in the present embodiment, owing to the reflecting portion 49, some of the secondary light 13b can be emitted from the second emitting portion 45b without entering the light converting member 43 again. Thus, in the present embodiment, the secondary light 13b can be more efficiently used.

In the present embodiment, owing to the indented portion 51a, the distribution of the primary light 13a can be expanded, and the primary light 13a can be used as illumination light. In the present embodiment, owing to the indented portion 51a having an irregular height and arrangement, it is possible to prevent the primary light 13a from being emitted in a particular direction alone. In other words, in the present embodiment, the primary light 13a can be dispersed. Thus, in the present embodiment, the primary light 13a can be evenly applied to the illumination target 15 as illumination light.

In the present embodiment, owing to the optical characteristics of the light transmitting member 47, the primary light 13a and the secondary light 13b can be efficiently transmitted through the light transmitting member 47, and can be efficiently applied to the illumination target 15 as illumination light.

In the present embodiment, when the reducing portion 51 is not provided and when the second emitting portion 45b is flat, the light converting member 43 needs to be provided apart from the primary light emitting portion 25 and the primary light entrance portion 41 so that the primary light 13*a* is fully applied to the rear surface 43*a* of the light converting member 43. That is, the relative positions of the light converting member 43, the primary light emitting portion 25, and the primary light entrance portion 41 need to be strictly set. Moreover, the light converting member 43 needs to function as an angle increasing portion. However, in this case, the degree of freedom in the designing of the optical element 40 is reduced.

Furthermore, when the optical element 40 is formed, foreign objects such as dust may be mixed in the space between the primary light entrance portion 41 and the light converting member 43, or the relative positions of the primary light emitting portion 25 and the rear surface 43*a* of the light converting member 43 may be shifted. In this case, the primary light 13*a* is transmitted through the light transmitting member 47 out of the original Gaussian intensity distribution, more specifically, with a distribution shape including rays that are inclined relative to the optical axis 11. Alternatively, the primary light 13*a* is applied to a position off the center of the rear surface 47*a* of the light transmitting member 47, and some of the primary light 13*a* is emitted from the second emitting portion 45*b* in a near-parallel-light state. As a result, the primary light 13*a* is particularly applied to only part of the illumination target 15, and color shading of the illumination light is caused.

However, in the present embodiment, owing to the reducing portion 51, the relative positions of the light converting member 43, the primary light emitting portion 25, and the primary light entrance portion 41 do not need to be strictly set, and the light converting member 43 does not need to function as the angle increasing portion, so that the degree of freedom in the designing of the optical element 40 can be improved.

In the present embodiment, even if foreign objects are mixed in and the relative positions are shifted, the reducing portion 51 makes it possible to prevent the primary light 13*a* from being particularly applied to only part of the illumination target 15, and color shading of the illumination light can be prevented. In other words, in the present embodiment, owing to the reducing portion 51, it is not necessary to create an environment that prevents the mixture of foreign objects, and it is possible to eliminate the necessity of selecting a design and materials that do not shift the relative positions.

Thus, in the present embodiment, it is possible to easily produce the illumination apparatus 10 including the optical element 40 which can ensure sufficient efficiency of light usage.

The illumination apparatus 10 according to the present embodiment can also be used as, for example, an observation apparatus having an unshown imaging unit. In this case, illumination light is evenly applied to the illumination target 15, and it is therefore possible that the color of the illumination light may change. However, the above-mentioned imaging unit can sufficiently make up for this color change by adjusting color temperature.

In the present embodiment, the components included in the optical element 40 have concentric shapes around the optical axis 11, and are provided rotationally symmetrically with respect to the optical axis 11. Thus, in the present embodiment, fabrication is easy, and costs can be lower. Particularly in the present embodiment, components can be provided at low cost by cutting.

In the present embodiment, the primary light source 21 may include, for example, a xenon lamp, a metal halide lamp, an LED, a gas laser, and a solid-state laser.

In the present embodiment, the beam spot 17 may be substantially equal in size to or smaller than the rear surface 43*a* of the light converting member 43. In this case, the primary light 13*a* is efficiently converted to the secondary light 13*b* by the light converting member 43.

In the present embodiment, the reflecting portion 49 may be provided, for example, on the inner circumferential surface of the holding portion 60. In this case, it is preferable to deposit a reflective material on the inner circumferential surface of the holding portion 60, or plate the inner circumferential surface with the reflective material. Aluminum or silver is suitable for the reflective material.

In the present embodiment, the reflecting portion 49 has only to be provided at least partly on the outer circumferential surface of the light transmitting member 47 except for the primary light entrance portion 41 and the second emitting portion 45*b* and on the inner circumferential surface of the holding portion 60.

In the present embodiment, as shown in FIG. 4, the reducing portion 51 may also be formed in the first emitting portion 45*a*. When the reducing portion 51 is formed in the first emitting portion 45*a* and the second emitting portion 45*b*, the primary light 13*a* and the secondary light 13*b* are emitted so that their distributions are expanded.

In the present embodiment, the reducing portion 51 may be provided at least in the second emitting portion 45*b*.

[First Modification]

Figure 5A:
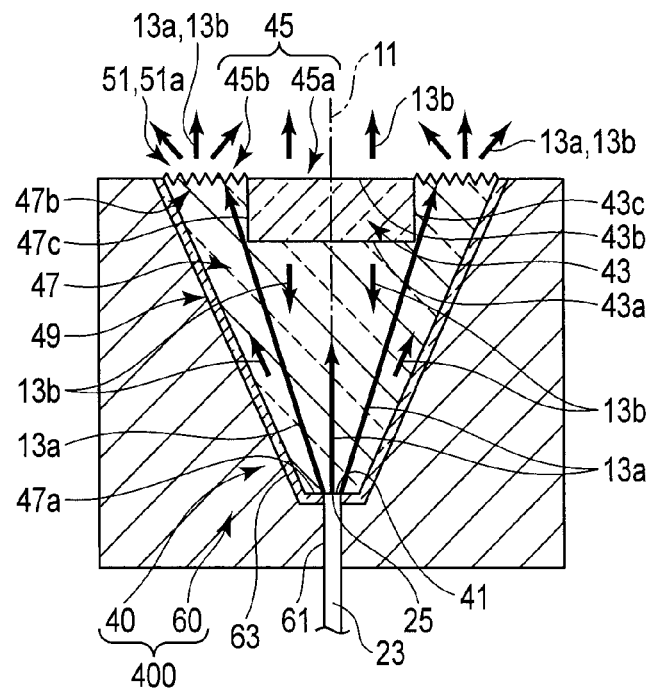
FIG. 5A is a diagram showing an example of the optical unit according to a first modification of the first embodiment.

The light transmitting member 47 may have a truncated cone shape shown in FIG. 5A, a semispherical dome shape shown in FIG. 5B, or a parabola shape shown in FIG. 5C. In this case, the shapes of the second hollow portion 63 and the reflecting portion 49 are appropriately set as desired in accordance with the shape of the light transmitting member 47.

[Second Modification]

Figure 6:
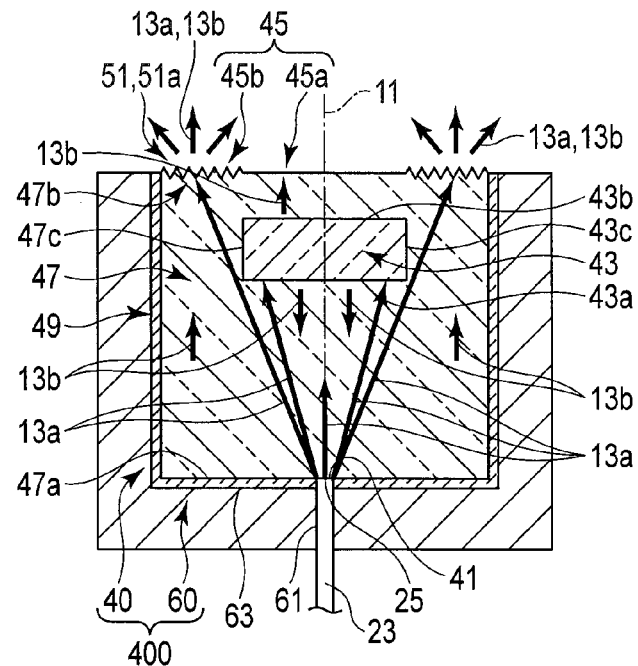
FIG. 6 is a schematic diagram of the optical unit according to a second modification of the first embodiment.

As shown in FIG. 6, the light transmitting member 47 has the light converting member 43 therein so that the light converting member 43 is buried in the light transmitting member 47 and so that the central axis of the light transmitting member 47 and the central axis of the light converting member 43 are provided on the optical axis 11. Thus, the light converting member 43 is provided inside the light transmitting member 47, and the light transmitting member 47 has the light converting member 43 therein. In this case, the secondary light 13*b* is emitted from the entire circumferential surface of the light converting member 43, and then transmitted through the light transmitting member 47, and emitted from the front surface 47*b* of the light transmitting member 47.

In this case, the illumination light emitting portion 45 has the first emitting portion 45*a*, and the second emitting portion 45*b* provided in a region other than the first emitting portion 45*a*. The second emitting portion 45*b* is provided in a region where is provided on the front surface 47*b* of the light transmitting member 47, the primary light 13*a* that has entered from the primary light entrance portion 41 travels straight via the light transmitting member 47 alone and can reach without entering any components other than the light transmitting member 47, such as the light converting member 43 and the reflecting portion 49. The reducing portion 51 is provided in at least the second emitting portion 45*b*, and has, for example, an annular belt shape (ring shape). It is important that the reducing portion 51 should be provided in the second emitting portion, so that the reducing portion 51 may be provided in the entire illumination light emitting portion 45. The first emitting portion 45*a* and the second emitting portion 45*b* are provided on the front surface 47*b* of the light transmitting member 47. The first emitting portion 45*a* is, for example, circularly provided around the center of the front surface 47*b*.

Thus, in the present modification, it is possible to prevent the light converting member 43 from coming off the light transmitting member 47. In the present modification, the light converting member 43 can efficiently radiate heat when emitting the secondary light 13b.

[Third Modification]

Figure 7:
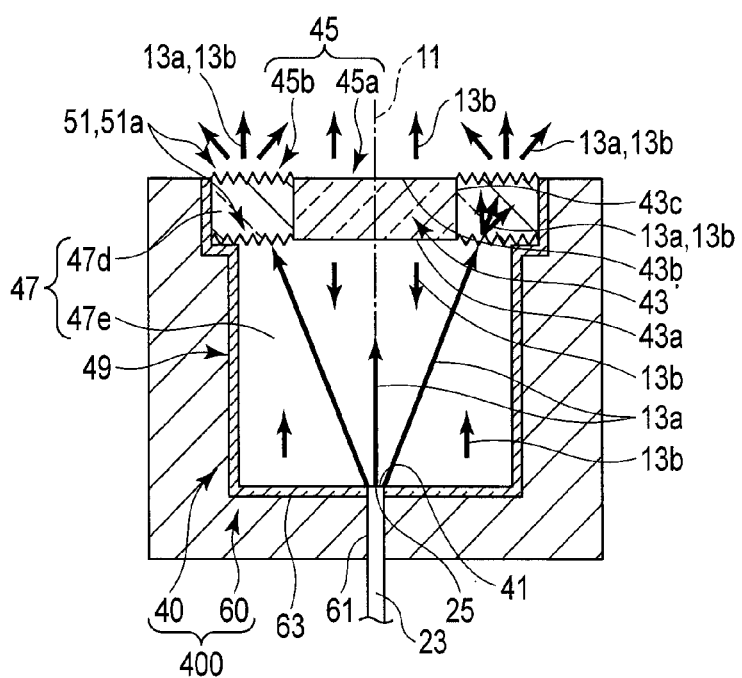
FIG. 7 is a schematic diagram of the optical unit according to a third modification of the first embodiment.

As shown in FIG. 7, the light transmitting member 47 is formed by an optically transparent member 47d which is held by the holding portion 60 and which is provided sideward to the light converting member 43, and a tightly closed portion 47e which is tightly closed by the light converting member 43, the transparent member 47d, and the holding portion 60 and which is filled with a fluid portion such as air.

The transparent member 47d has the same thickness as the light converting member 43. The transparent member 47d holds the light converting member 43 so that the front surface 43b of the light converting member 43 is flush with the front surface of the transparent member 47d, so that the rear surface 43a of the light converting member 43 is flush with the rear surface of the transparent member 47d, so that the central axis of the transparent member 47d and the central axis of the light converting member 43 are provided on the optical axis 11.

The transparent member 47d covers the whole opening portion of the second hollow portion 63. The rear surface of the transparent member 47d is in contact with the fluid portion filling the tightly closed portion 47e.

The transparent member 47d is made of, for example, optically transparent glass or an optically transparent resin.

The reducing portion 51 is provided, for example, on the front surface and rear surface of the transparent member 47d, and provided sideward to the light converting member 43.

In the present modification, the primary light 13a is applied to the transparent member 47d via the fluid portion filling the tightly closed portion 47e. The primary light 13a then enters the transparent member 47d while being scattered by the reducing portion 51 formed on the rear surface of the transparent member 47d, and is emitted while being further scattered by the reducing portion 51 formed on the front surface of the transparent member 47d. The primary light 13a is then applied to the illumination target 15 as illumination light.

Thus, in the present modification, there are many interfaces having the diffusion function, so that the primary light 13a can be sufficiently diffused to the outside (toward the illumination target 15), and the primary light 13a can be emitted so that the distribution of the primary light 13a is expanded.

[Fourth Modification]

Figure 8:
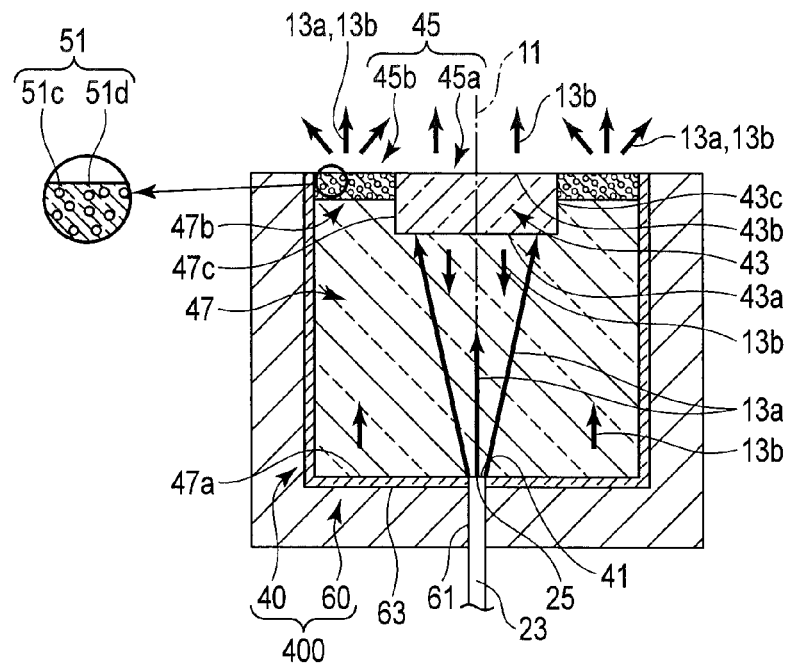
FIG. 8 is a schematic diagram of the optical unit according to a fourth modification of the first embodiment.

As shown in FIG. 8, the light converting member 43 is provided so that the front surface 43b of the light converting member 43 is provided to protrude frontward to the front surface 47b of the light transmitting member 47.

In this case, the reducing portion 51 is formed as a plate member having an annular belt shape (ring) separately from the light converting member 43 and the light transmitting member 47. The reducing portion 51 has a thickness equal to the protruding amount of the front surface 43b of the light converting member 43 from the front surface 47b of the light transmitting member 47 so that the front surface of the reducing portion 51 is flush with the front surface 43b of the light converting member 43. The reducing portion 51 surrounds the light converting member 43 so that the inner circumferential surface of the reducing portion 51 is in close contact with the side surface 43c of the light converting member 43 and so that the front surface of the reducing portion 51 is flush with the first emitting portion 45a. The reducing portion 51 is provided on the front surface 47b of the light transmitting member 47 so that it optically connected to the front surface 47b of the light transmitting member 47.

The reducing portion 51 has, for example, a diffusing member which does not emit the primary light 13a in a near-parallel-light state, but sufficiently diffuses the primary light 13a to the outside (toward the illumination target 15) and emits the primary light 13a so that the distribution of the primary light 13a is expanded. The reducing portion 51 has the second emitting portion 45b which functions as the front surface of the reducing portion 51.

The reducing portion 51 has minute particles 51c and a transparent member 51d for the diffusion of the primary light 13a. The particles 51c are dispersed in the transparent member 51d. The particles 51c and the transparent member 51d are optically transparent to visible light, and are different in refractive index from each other.

For example, the transparent member 51d is made of, for example, optically transparent glass or an optically transparent resin.

The minute particles 51c have a higher refractive index than the transparent member 51d. Such particles 51c are, for example, aluminum oxide.

[Advantageous Effects]

In the present modification, the effort for forming the indented portion 51a can be reduced by the plate-shaped reducing portion 51. Moreover, according to the present modification, in the reducing portion 51, the particles 51c are properly selected, the concentration of the particles 51c is controlled, and the dispersion of the particles 51c is controlled. This ensures a micro light distribution.

In the present modification, the reducing portion 51 may be provided frontward to the first emitting portion 45a as long as the reducing portion 51 does not block the secondary light 13b and does not reverse the secondary light 13b rearward.

[Fifth Modification]

Figure 9:
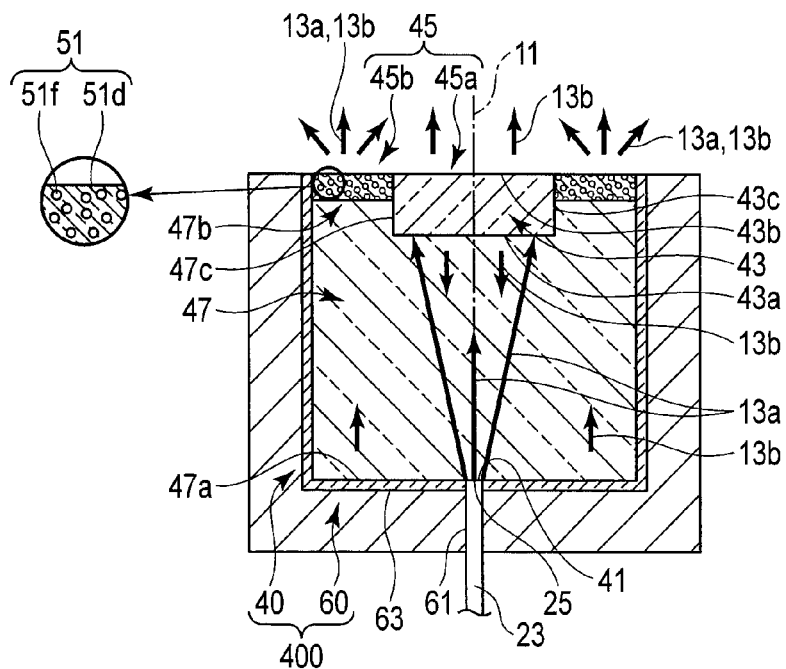
FIG. 9 is a schematic diagram of the optical unit according to a fifth modification of the first embodiment.

As shown in FIG. 9, the reducing portion 51 is formed by, for example, the dispersion of minute particles 51f which convert the optical characteristics of the primary light 13a in the transparent member 51d so that the primary light 13a is diffused. That is, the reducing portion 51 has a function of converting the wavelength of, for example, the primary light 13a.

The particles 51f absorb the primary light 13a, convert the wavelength of the absorbed primary light 13a to a wavelength different from the wavelength of the primary light 13a, and generate light having this wavelength. This light may be the secondary light 13b, or tertiary light different in wavelength from the primary light 13a and the secondary light 13b.

[Advantageous Effects]

In the present modification, advantageous effects similar to the advantageous effects according to the fourth modification can be obtained.

Moreover, in the present modification, the primary light 13a is isotropically emitted by the wavelength conversion, which ensures that color shading of the illumination light can be prevented.

[Second Embodiment]

Figure 10A:
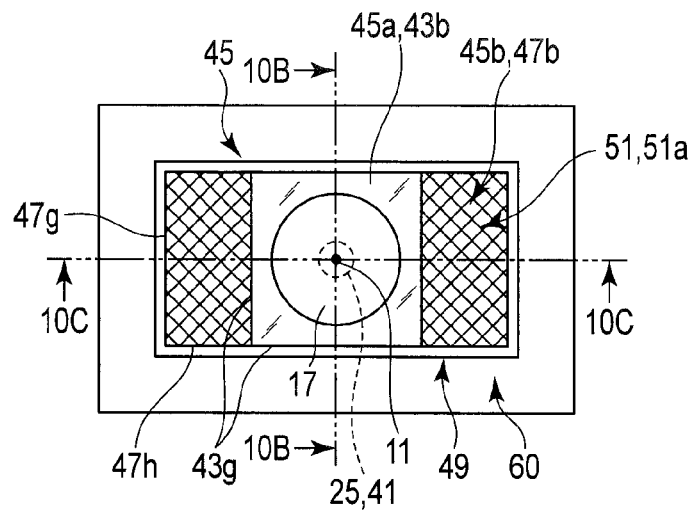
FIG. 10A is a diagram of an optical unit according to a second embodiment viewed from the illumination light emission side.
Figure 10B:
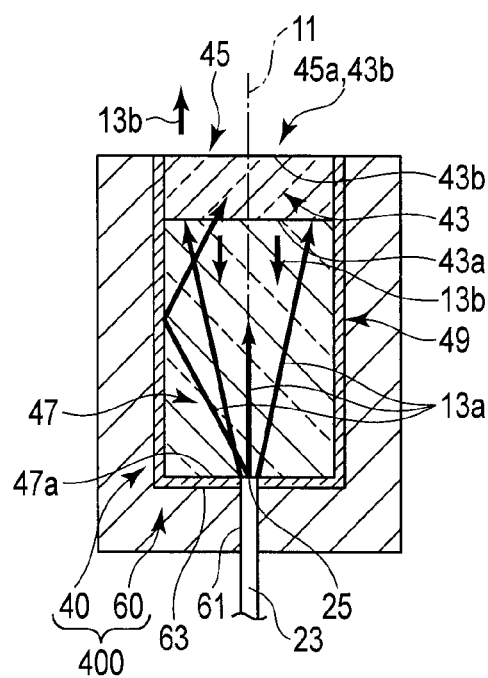
FIG. 10B is a sectional view taken along the line 10B-10B shown in FIG. 10A.
Figure 10C:
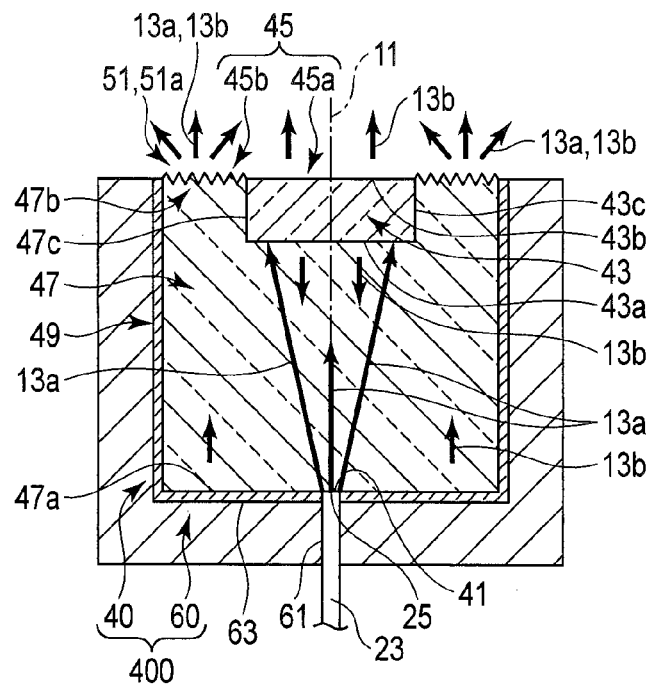
FIG. 10C is a sectional view taken along the line 10C-10C shown in FIG. 10A.

As shown in FIG. 10A, FIG. 10B, and FIG. 10C, the light converting member 43 has a square column shape. More specifically, the light converting member 43 has a columnar shape so that at least the rear surface 43a and the front surface 43b have square shapes equal in size to each other.

As shown in FIG. 10A, FIG. 10B, and FIG. 10C, the original form of the light transmitting member 47 has a rectangular columnar shape. More specifically, the light transmitting member 47 has a columnar shape such that at least the rear surface 47a and the front surface 47b have rectangular shapes equal in size to each other and such that two side surfaces facing each other have rectangular shapes. As shown in FIG. 10A, a short side 47g of the rectangular front surface 47b has the same length as one side 43g of the front surface 43b of the square light converting member 43. Thus, the side 43g of the light converting member 43 is in contact with a long side 47h of the front surface 47b, and part of the light converting member 43 abuts on the reflecting portion 49.

The light converting member 43 is provided in the light transmitting member 47 as in the first embodiment.

The second emitting portion 45b and the reducing portion 51 have rectangular shapes.

The beam spot 17 is smaller than the rear surface 43a.

[Advantageous Effects]

In the present embodiment, the brightness of the illumination light can be improved by the sneak-through effects, and the easiness of manufacture of the optical element 40 and the degree of freedom in design of the optical element 40 can be improved by color shading reducing effects.

In the present embodiment, the front surface 47b and the long side 47h of the light transmitting member 47 abut on the side 43g of the front surface 43b of the light converting member 43, and the reflecting portion 49 is provided. Therefore, in the present embodiment, some of the primary light 13a is repeatedly reflected toward the light converting member 43 by the reflecting portion 49. Thus, in the present embodiment, the primary light 13a as the illumination light can be suppressed, and a great amount of the secondary light 13b as the illumination light can be emitted.

In the present embodiment, the front surface 47b and the long side 47h of the light transmitting member 47 abut on the side 43g of the front surface 43b of the light converting member 43, and the light converting member 43 abuts on the reflecting portion 49. Thus, in the present embodiment, even if the beam spot 17 is larger than the rear surface 43a in a direction along the short side 47g, the primary light is reflected by the reflecting portion 49, the primary light does not escape, and the escape amount of the primary light can be reduced.

In the present embodiment as well as in the first embodiment, even if the beam spot 17 is larger than the rear surface 43a, the primary light 13a can be sufficiently diffused to the outside (toward the illumination target 15), and the primary light 13a can be emitted so that the distribution of the primary light 13a is expanded, owing to the reducing portion 51. Thus, in the present embodiment, the density of the primary light 13a can be reduced, and the primary light 13a can be evenly applied to the illumination target 15 as illumination light.

Accordingly, in the present embodiment, the degree of freedom in the designing of the optical element 40 can be improved. The rear surface 47a and the front surface 47b may have elliptic shapes, and the rear surface 43a and the front surface 43b may have elliptic shapes. In this case, part of the circumferential surface of the light converting member 43 is in abutment with part of the circumferential surface of the light transmitting member 47.

[First Modification]

Figure 11A:
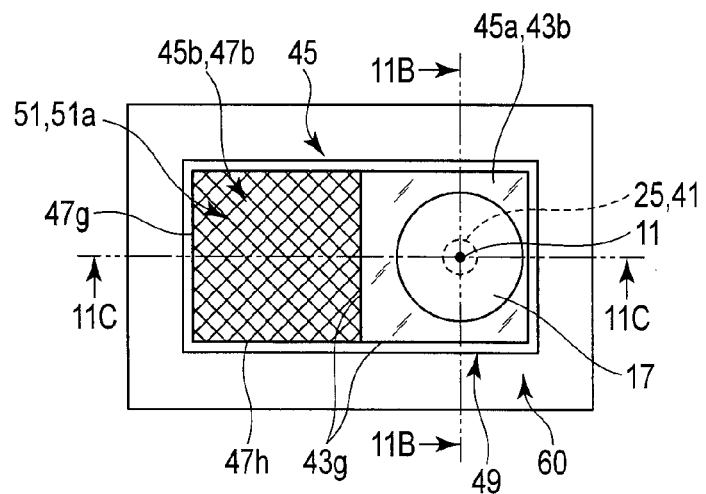
FIG. 11A is a diagram of the optical unit according to the first modification of the second embodiment viewed from the illumination light emission side.

As shown in FIG. 11A, FIG. 11B, and FIG. 11C, the central axis of the light converting member 43 is provided off the central axis of the light transmitting member 47 so that the short side 47g of the front surface 47b of the light transmitting member 47 abuts on the side 43g of the front surface 43b of the light converting member 43.

Moreover, the central axis of the light converting member 43 and the central axis of the light transmitting member 47 are provided off the optical axis 11. Thus, the central axis of the beam spot 17 is provided closer to the short side 47g (the right side in FIG. 11A) on which the light converting member 43 abuts, with respect to the central axis of the rear surface 43a.

[Advantageous Effects]

In the present modification, even if the distribution of the primary light 13a is suddenly disturbed, the reflecting portion 49 reliably reflects the primary light 13a to the light converting member 43. Thus, in the present modification, color shading can be prevented.

[Third Embodiment]

Figure 12:
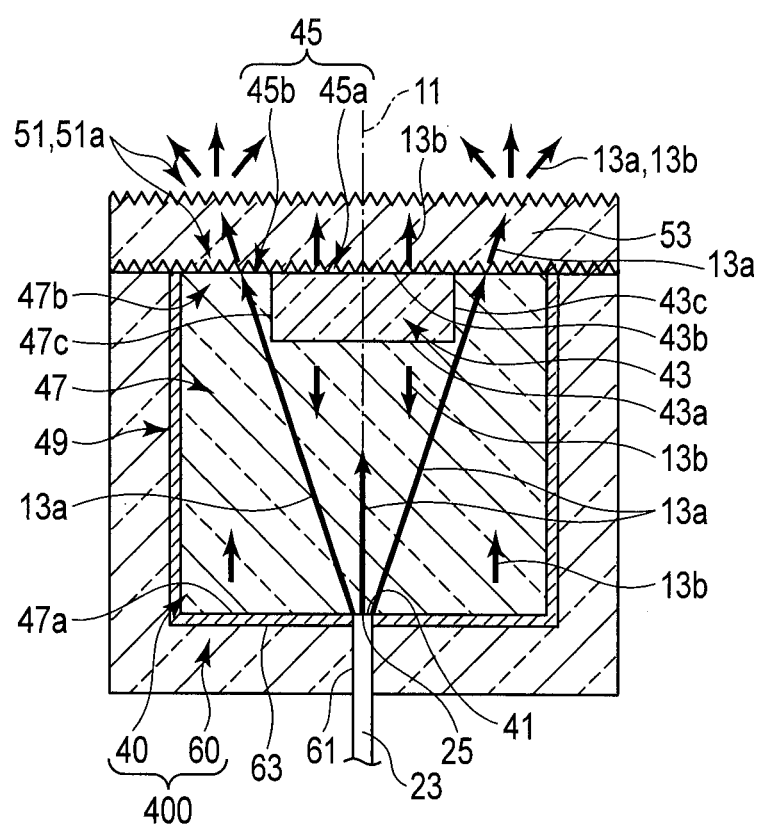
FIG. 12 is a schematic diagram of an optical unit according to a third embodiment.

As shown in FIG. 12, in the present embodiment, a plate-shaped light transmitting member 53 separate from the light transmitting member 47 is additionally provided. The light transmitting member 53 has optical characteristics similar to, for example, the optical characteristics of the light transmitting member 47. The light transmitting member 53 is provided at least on the entire front surface 43b side of the light converting member 43 and on the entire front surface 47b side of the light transmitting member 47 so that the rear surface of the light transmitting member 53 is close to the front surface 43b of the light converting member 43 and the front surface 47b of the light transmitting member 47. The light transmitting member 53 is provided, for example, on the outer circumferential surface side of the holding portion 60.

The second emitting portion 45b is provided on the front surface 47b of the light transmitting member 47. The reducing portion 51 is provided on the entire rear surface and the entire front surface of the light transmitting member 53. Therefore, the reducing portion 51 is provided frontward to the second emitting portion 45b.

[Advantageous Effects]

Thus, in the present embodiment, the light transmitting member 53 is separate from the light transmitting member 47, so that the structure can be simpler, and manufacture at lower cost is possible.

The light transmitting member 53 in which the reducing portion 51 is provided is not particularly limited as long as the light transmitting member 53 is separate from the light transmitting member 47 and is provided in a part where the primary light 13a is applied. The light transmitting member 53 has only to be formed in the whole portion region where the primary light 13a directly travels on the front surface 43b of the light converting member 43 and the front surface 47b of the light transmitting member 47. In this case, the light transmitting member 53 has, for example, an annular belt shape (ring shape).

[First Modification]

Figure 13:
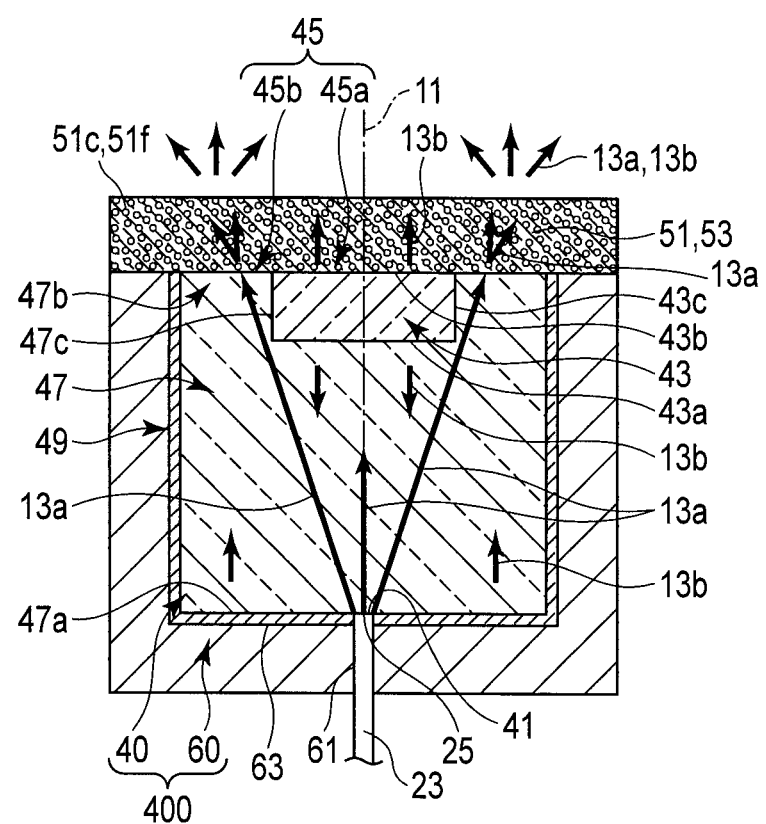
FIG. 13 is a diagram of the optical unit according to a first modification of the third embodiment.

As shown in FIG. 13, the light transmitting member 53 may have therein a material which scatters the primary light 13a and which functions as the reducing portion 51. This material is represented by, for example, the particles 51c and 51f.

The present invention is not completely limited to the embodiments described above, and modifications of components can be made at the stage of carrying out the invention without departing from the spirit thereof. Further, various inventions can be made by properly combining the components disclosed in the embodiments described above.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An illumination apparatus comprising a light source unit which emits primary light, and an optical unit which functions when the primary light emitted from the light source unit is applied to the optical unit, the light source unit comprising a primary light emitting portion which emits the primary light to the optical unit,
the optical unit comprising:
a primary light entrance portion which is optically connected to the primary light emitting portion and which the primary light emitted from the primary light emitting portion enters;
a light converting member which is provided apart from the primary light entrance portion, the light converting member converting the optical characteristics of the primary light entering from the primary light entrance portion when the primary light is applied to the light converting member, the light converting member generating secondary light different from the primary light;
an illumination light emitting portion which emits at least one of the primary light and the secondary light to an outside as illumination light;
the central axis of the primary light emitted by the primary light emitting portion being referred to as an optical axis,
the side of the primary light emitting portion in an optical axis direction being referred to as rearward,
the side of the light converting member in the optical axis direction being referred to as frontward,
a direction that intersects at right angles with the optical axis being referred to as sideward,
a light transmitting member which is provided between the primary light entrance portion and the light converting member and which is also at least partly continuously provided from the primary light entrance portion to the illumination light emitting portion so that the primary light and the secondary light is transmitted therethrough;
a reflecting portion which is provided on a circumferential surface of the light transmitting member including the light converting member and which reflects the primary light and the secondary light; and
a reducing portion which is directly provided in the illumination light emitting portion or provided frontward to part of the illumination light emitting portion and which reduces the density of the primary light as the illumination light emitted from the illumination light emitting portion.

2. The illumination apparatus according to claim 1, wherein the reducing portion functions as an angle increasing portion which increases the emission angle of the primary light.

3. The illumination apparatus according to claim 2, wherein the illumination light emitting portion comprises a first emitting portion, and a second emitting portion provided in a region other than the first emitting portion,
the region in which the second emitting portion is provided comprises a region which is provided in the light transmitting member and where the primary light that has entered from the primary light entrance portion enters straight via the light transmitting member alone and can reach without entering any components other than the light transmitting member, and
the reducing portion directly provided in the illumination light emitting portion is provided in at least the second emitting portion.

4. The illumination apparatus according to claim 3, wherein the reducing portion is provided in the second emitting portion, or provided frontward to the second emitting portion, or provided sideward to the light converting member.

5. The illumination apparatus according to claim 4, wherein the reducing portion has an indented portion, and
the indented portion is formed with a regular height and arrangement or formed with an irregular height and arrangement.

6. The illumination apparatus according to claim 5, wherein the indented portion has a grating structure.

7. The illumination apparatus according to claim 5, wherein the indented portion has a microlens group.

8. The illumination apparatus according to claim 4, wherein the reducing portion comprises particles and a transparent member which are transparent to visible light and which are different in refractive index from each other as regards diffusion of the primary light, and
the particles are dispersed in the transparent member.

9. The illumination apparatus according to claim 4, wherein the reducing portion has a function of converting the wavelength of the primary light.

10. The illumination apparatus according to claim 4, wherein the light converting member comprises an application surface which is a plane provided to intersect at right angles with the optical axis and to which the primary light is applied,
an application region of the primary light projected on the plane that intersects at right angles with the optical axis including the application surface is referred to as a beam spot, and
the light converting member is provided apart from the primary light entrance portion so that the beam spot is formed to be substantially the same as the application surface or to be larger than the application surface.

11. The illumination apparatus according to claim 4, wherein part of the light converting member abuts on the reflecting portion.

12. The illumination apparatus according to claim 11, wherein the light converting member comprises an application surface which is a plane provided to intersect at right angles with the optical axis and to which the primary light is applied,
an application region of the primary light projected on the plane that intersects at right angles with the optical axis including the application surface is referred to as a beam spot, and
the center of the beam spot is provided closer to the side where part of the light converting member abuts on the reflecting portion with respect to the center of the application surface.

* * * * *